United States Patent
Kirihara et al.

(10) Patent No.: US 9,339,496 B2
(45) Date of Patent: May 17, 2016

(54) COMPOSITION FOR TREATING OR PREVENTING GLAUCOMA COMPRISING A SULFONAMIDE COMPOUND, AND A BETA-RECEPTOR ANTAGONIST

(71) Applicant: SANTEN PHARMACEUTICAL CO., LTD., Osaka-shi, Osaka (JP)

(72) Inventors: Tomoko Kirihara, Ikoma (JP); Atsushi Shimazaki, Ikoma (JP); Masatsugu Nakamura, Ikoma (JP)

(73) Assignee: SANTEN PHARMACEUTICAL CO., LTD., Osaka (JP)

( * ) Notice: Subject to any disclaimer, the term of this patent is extended or adjusted under 35 U.S.C. 154(b) by 7 days.

(21) Appl. No.: 13/939,381

(22) Filed: Jul. 11, 2013

(65) Prior Publication Data

US 2014/0018396 A1     Jan. 16, 2014

Related U.S. Application Data

(60) Provisional application No. 61/671,219, filed on Jul. 13, 2012.

(51) Int. Cl.
| | |
|---|---|
| *A61K 31/444* | (2006.01) |
| *A61K 45/06* | (2006.01) |
| *C07D 401/14* | (2006.01) |
| *A61K 31/498* | (2006.01) |
| *A61K 31/5377* | (2006.01) |
| *A61K 31/542* | (2006.01) |
| *A61K 31/5575* | (2006.01) |

(52) U.S. Cl.
CPC ............ *A61K 31/444* (2013.01); *A61K 31/498* (2013.01); *A61K 31/5377* (2013.01); *A61K 31/542* (2013.01); *A61K 31/5575* (2013.01); *A61K 45/06* (2013.01); *C07D 401/14* (2013.01)

(58) Field of Classification Search
None
See application file for complete search history.

(56) References Cited

U.S. PATENT DOCUMENTS

2008/0045545 A1*   2/2008   Prasanna et al. .............. 514/256
2012/0190852 A1*   7/2012   Hagihara et al. .............. 544/333

FOREIGN PATENT DOCUMENTS

| WO | WO 2004/019951 A1 | 3/2004 |
|---|---|---|
| WO | WO 2004/045644 A1 | 6/2004 |
| WO | WO 2010/113957 A1 | 10/2010 |

OTHER PUBLICATIONS

Timolol Ophthalmic (Medline Plus, http://www.nlm.nih.gov/medlineplus/druginfo/meds/a682043.html.*
Higginbotham ("Considerations in glaucoma therapy: fixed combinations versus their component medications." Clinical Ophthalmology. 2010; 4:1-9).*
Glaucol Patient information Leaflet (Steripak Ltd, Dec. 2011).*
Berenbaum (Pharmacological Reviews, 1989).*
U.S. Appl. No. 13/982,437, filed Jul. 11, 2013; confirmation No. 3025.

* cited by examiner

*Primary Examiner* — Marcos Sznaidman
*Assistant Examiner* — Rayna B Rodriguez
(74) *Attorney, Agent, or Firm* — Holtz, Holtz & Volek PC

(57) ABSTRACT

A composition for treating or preventing glaucoma or ocular hypertension including a isopropyl (6-{[4-(pyrazol-1-yl)benzyl](pyridin-3-ylsulfonyl)aminomethyl}pyridin-2-ylamino) acetate and a beta-receptor antagonist, in a combined pharmaceutically acceptable amount. As for the administration form, these drugs may be administered concomitantly or may be administered as a combination drug.

17 Claims, No Drawings

COMPOSITION FOR TREATING OR PREVENTING GLAUCOMA COMPRISING A SULFONAMIDE COMPOUND, AND A BETA-RECEPTOR ANTAGONIST

CROSS-REFERENCE TO RELATED APPLICATIONS

This application claims the benefit of U.S. Provisional Application No. 61/671,219 filed Jul. 13, 2012, the entire contents of which are incorporated by reference herein.

TECHNICAL FIELD

The present invention relates to a preventive or therapeutic agent for glaucoma or ocular hypertension, or an intraocular pressure lowering agent comprising a combination of isopropyl (6-{[4-(pyrazol-1-yl)benzyl](pyridin-3-ylsulfonyl)aminomethyl}pyridin-2-ylamino) acetate with other preventive or therapeutic drug for glaucoma or ocular hypertension.

BACKGROUND ART

Glaucoma is an intractable ocular disease with a risk of blindness, involving an increase in intraocular pressure due to various predisposing factors and the disorder of internal tissues of eyeballs (retina, an optic nerve, and the like). A general method of treating glaucoma is intraocular pressure lowering therapy, which is exemplified by pharmacotherapy, laser therapy, surgical therapy, and the like.

In the pharmacotherapy, a drug such as a sympathomimetic drug (a nonselective stimulant such as dipivefrin or an $\alpha_2$-receptor agonist such as brimonidine), a sympatholytic drug (a $\beta$-receptor antagonist such as timolol, befunolol, carteolol, nipradilol, betaxolol, levobunolol or metipranolol, or an $\alpha_1$-receptor antagonist such as bunazosin hydrochloride), a parasympathomimetic drug (such as pilocarpine), a carbonic anhydrase inhibitor (such as acetazolamide), a prostaglandin (such as isopropyl unoprostone, latanoprost, travoprost or bimatoprost) is used. Further, Rho-kinase inhibitors (such as SNJ-1656), adenosine agonists (such as INO-8875), serotonin antagonists (BVT-28949), and the like have been under development as novel drugs. Other than these, a prostaglandin E2 receptor subtype 2 agonist (EP2 agonist) is known to have an intraocular pressure lowering effect, and it is reported in WO 2010/113957 that a sulfonamide compound having high EP2 receptor selectivity and a potent EP2 agonistic activity is promising as a therapeutic drug for glaucoma.

There are several reports of the combined use of drugs having an intraocular pressure lowering effect to treat glaucoma. For example, Japanese Patent No. 2726672 reports the combined administration of a sympatholytic drug with a prostaglandin. WO 2002/38158 discloses a method of treating glaucoma by the combined administration of several drugs having an intraocular pressure lowering effect to eyes. WO 2004/019951 reports the combined administration of a Rho-kinase inhibitor with a prostaglandin, and WO 2004/045644 reports the combined administration of a Rho-kinase inhibitor with a $\beta$-receptor antagonist.

However, there have been no reports specifically disclosing a combination of isopropyl (6-{[4-(pyrazol-1-yl)benzyl](pyridin-3-ylsulfonyl)aminomethyl}pyridin-2-ylamino)acetate, which has a high EP2 receptor selectivity and a potent EP2 agonistic activity, with other preventive or therapeutic drug for glaucoma or ocular hypertension, and naturally, it has not been known at all as to what effect of such a combination is exerted on the intraocular pressure.

SUMMARY OF THE INVENTION

Problems that the Invention is to Solve

It is a very interesting subject to discover a combination of preventive or therapeutic drugs for glaucoma or ocular hypertension, which is useful as a preventive or therapeutic agent for glaucoma or ocular hypertension.

Means for Solving the Problems

The present inventors made intensive studies on the effect of a combination of preventive or therapeutic agents for glaucoma or ocular hypertension, and as a result, they found that by combining isopropyl (6-{[4-(pyrazol-1-yl)benzyl](pyridin-3-ylsulfonyl) aminomethyl}pyridin-2-ylamino)acetate with other preventive or therapeutic agent for glaucoma or ocular hypertension, the intraocular pressure lowering effect is enhanced as compared with the case where each agent is used singly, and thus completed the invention. That is, the invention relates to the following aspects.

(1) A preventive or therapeutic agent for glaucoma or ocular hypertension, comprising a combination of isopropyl (6-{[4-(pyrazol-1-yl)benzyl](pyridin-3-ylsulfonyl) aminomethyl}pyridin-2-ylamino)acetate with one or more other preventive or therapeutic drugs for glaucoma or ocular hypertension (with the proviso that tafluprost is excluded).

(2) An intraocular pressure lowering agent, comprising a combination of isopropyl (6-{[4-(pyrazol-1-yl)benzyl](pyridin-3-ylsulfonyl)aminomethyl}pyridin-2-ylamino)acetate with one or more other preventive or therapeutic drugs for glaucoma or ocular hypertension (with the proviso that tafluprost is excluded).

(3) The preventive or therapeutic agent or the intraocular pressure lowering agent according to the above (1) or (2), wherein the other preventive or therapeutic drug for glaucoma or ocular hypertension (with the proviso that tafluprost is excluded) is one or more preventive or therapeutic agents selected from the group consisting of a nonselective sympathomimetic drug, an $\alpha_2$-receptor agonist, an $\alpha_1$-receptor antagonist, a $\beta$-receptor antagonist, a parasympathomimetic drug, a carbonic anhydrase inhibitor, a prostaglandin and a Rho-kinase inhibitor.

(4) The preventive or therapeutic agent or the intraocular pressure lowering agent according to the above (3), wherein the nonselective sympathomimetic drug is dipivefrin.

(5) The preventive or therapeutic agent or the intraocular pressure lowering agent according to the above (3) or (4), wherein the $\alpha_2$-receptor agonist is brimonidine or apraclonidine.

(6) The preventive or therapeutic agent or the intraocular pressure lowering agent according to any one of the above (3) to (5), wherein the $\alpha_1$-receptor antagonist is bunazosin.

(7) The preventive or therapeutic agent or the intraocular pressure lowering agent according to any one of the above (3) to (6), wherein the $\beta$-receptor antagonist is timolol, befunolol, carteolol, nipradilol, betaxolol, levobunolol or metipranolol.

(8) The preventive or therapeutic agent or the intraocular pressure lowering agent according to any one of the above (3) to (7), wherein the parasympathomimetic drug is pilocarpine.

(9) The preventive or therapeutic agent or the intraocular pressure lowering agent according to any one of the above (3) to (8), wherein the carbonic anhydrase inhibitor is dorzolamide, brinzolamide or acetazolamide.

(10) The preventive or therapeutic agent or the intraocular pressure lowering agent according to any one of the above (3) to (9), wherein the prostaglandin is isopropyl unoprostone, latanoprost, travoprost or bimatoprost.

(11) The preventive or therapeutic agent or the intraocular pressure lowering agent according to any one of the above (3) to (10), wherein the Rho-kinase inhibitor is (R)-trans-N-(pyridin-4-yl)-4-(1-aminoethyl)cyclohexanecarboxamide, (R)-(+)-N-(1H-pyrrolo[2,3-b]pyridin-4-yl)-4-(1-aminoethyl)-benzamide, 1-(5-isoquinolinesulfonyl)homopiperazine or 1-(5-isoquinolinesulfonyl)-2-methylpiperazine.

Incidentally, from the above-described respective configurations (1) to (11), one or more configurations can be arbitrarily selected and combined.

Herein after in the specification, "the other preventive or therapeutic drugs for glaucoma or ocular hypertension" means "the other preventive or therapeutic drugs for glaucoma or ocular hypertension except for tafluprost"

Advantage of the Invention

By the combined administration of isopropyl (6-{[4-(pyrazol-1-yl)benzyl](pyridin-3-ylsulfonyl)aminomethyl}pyridin-2-ylamino) acetate with one or more other preventive or therapeutic drug for glaucoma or ocular hypertension to eyes, the intraocular pressure lowering effect is enhanced. Therefore, the invention is useful as a preventive or therapeutic agent for glaucoma or ocular hypertension or an intraocular pressure lowering agent.

MODE FOR CARRYING OUT THE INVENTION

The invention is directed to a preventive or therapeutic agent for glaucoma or ocular hypertension or an intraocular pressure lowering agent, comprising a combination of isopropyl (6-{[4-(pyrazol-1-yl)benzyl](pyridin-3-ylsulfonyl)aminomethyl}pyridin-2-ylamino) acetate (hereinafter also referred to as "present compound") represented by the following formula (1) with one or more other preventive or therapeutic drugs for glaucoma or ocular hypertension, where these drugs complement and/or enhance their intraocular pressure lowering effects each other.

III

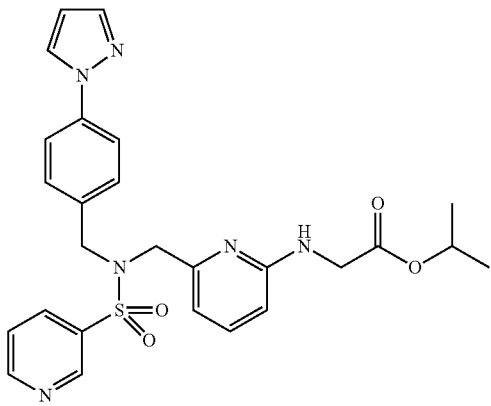

The present compound in the invention can be synthesized by the method described in WO 2009/113600 or WO 2010/113957.

The invention is characterized in that glaucoma or ocular hypertension is prevented or treated by administering a combination of the present compound with other preventive or therapeutic drug for glaucoma or ocular hypertension. Glaucoma in the invention includes primary open angle glaucoma, normal tension glaucoma, hypersecretion glaucoma, ocular hypertension, acute angle-closure glaucoma, chronic angle-closure glaucoma, combined-mechanism glaucoma, steroid-induced glaucoma, amyloid glaucoma, neovascular glaucoma, malignant glaucoma, capsular glaucoma, plateau iris syndrome and the like.

In the invention, the combination of the present compound with one or more other preventive or therapeutic drugs for glaucoma or ocular hypertension is preferably a combination of the present compound with one to three other preventive or therapeutic drugs for glaucoma or ocular hypertension, and more preferably a combination of the present compound with one or two other preventive or therapeutic drugs for glaucoma or ocular hypertension.

The other preventive or therapeutic drug for glaucoma or ocular hypertension in the invention may be any as long as the drug has an intraocular pressure lowering effect and is useful for treating glaucoma, and examples thereof include a non-selective sympathomimetic drug, an $\alpha_2$-receptor agonist, an $\alpha_1$-receptor antagonist, a β-receptor antagonist, a parasympathomimetic drug, a carbonic anhydrase inhibitor, a prostaglandin, a Rho-kinase inhibitor and the like. In the case where the present compound is combined with two other preventive or therapeutic drugs for glaucoma or ocular hypertension, the two other preventive or therapeutic drugs for glaucoma or ocular hypertension are preferably two preventive or therapeutic agents selected from the group consisting of a β-receptor antagonist, a carbonic anhydrase inhibitor and a prostaglandin, and more preferably a β-receptor antagonist and a carbonic anhydrase inhibitor, or a β-receptor antagonist and a prostaglandin.

Specific examples of the nonselective sympathomimetic drug include dipivefrin. Specific examples of the $\alpha_2$-receptor agonist include brimonidine and apraclonidine. Specific examples of the $\alpha_1$-receptor antagonist include bunazosin. Specific examples of the β-receptor antagonist include timolol, befunolol, carteolol, nipradilol, betaxolol, levobunolol and metipranolol. Specific examples of the parasympathomimetic drug include pilocarpine. Specific examples of the carbonic anhydrase inhibitor include dorzolamide, brinzolamide and acetazolamide.

Specific examples of the prostaglandin include prostaglandins disclosed in JP-A-59-1418 (particularly, a natural prostaglandin such as prostaglandin F2α), prostaglandins such as latanoprost disclosed in JP-T-3-501025, prostaglandins such as isopropyl unoprostone disclosed in JP-A-2-108, prostaglandins such as bimatoprost disclosed in JP-T-8-501310, prostaglandins such as travoprost disclosed in JP-A-10-182465, prostaglandins such as AL-6598 disclosed in Surv Opthalmol 47 (Suppl 1): S13-S33, 2002, and prostaglandins such as PF-04475270 disclosed in Exp Eye Res. 89: 608-17, 2009. Among these, the prostaglandin is preferably PGF2α or a PGF2α derivative, more preferably isopropyl unoprostone, latanoprost, travoprost or bimatoprost.

The Rho-kinase inhibitor in the invention refers to a compound which inhibits serine/threonine kinase activated with the activation of Rho. Examples of such a compound include compounds which inhibit ROKα (ROCK-II), p160ROCK (ROKβ, ROCK-I) or other proteins having a serine/threonine kinase activity. Specific examples of the Rho-kinase inhibitor include Rho-kinase inhibitors such as (R)-trans-N-(pyridin-4-yl)-4-(1-aminoethyl)cyclohexanecarboxamide and (R)-(+)-N-(1H-pyrrolo[2,3-b]pyridin-4-yl)-4-(1-aminoethyl)benzamide disclosed in WO 98/06433 and WO 00/09162, Rho-kinase inhibitors such as 1-(5-isoquinolinesulfonyl)homopiperazine and 1-(5-isoquinolinesulfonyl)-2-methylpiperazine disclosed in WO 97/23222 and Nature, 389, 990-994 (1997), Rho-kinase inhibitors such as (1-benzylpyrrolidin-3-yl)-(1H-indazol-5-yl)amine disclosed in WO 01/56988, Rho-kinase inhibitors such as (1-benzylpiperidin-4-yl)-(1H-indazol-5-yl)amine disclosed in WO 02/100833, Rho-kinase inhibitors such as N-[2-(4-fluorophenyl)-6,7-dimethoxy-4-quinazolinyl]-N-(1H-indazol-5-yl)amine disclosed in WO 02/076976, Rho-kinase inhibitors such as N-4-(1H-indazol-5-yl)-6,7-dimethoxy-N-2-pyridin-4-yl-quinazolin-2,4-diamine disclosed in WO 02/076977, and Rho-kinase inhibitors such as 4-methyl-5-(2-methyl-[1,4]diazepan-1-sulfonyl)isoquinoline disclosed in WO 99/64011. Among these, particularly, (R)-trans-N-(pyridin-4-yl)-4-(1-aminoethyl)cyclohexanecarboxamide, (R)-(+)-N-(1H-pyrrolo[2,3-b]pyridin-4-yl)-4-(1-aminoethyl)benzamide, 1-(5-isoquinolinesulfonyl)homopiperazine or 1-(5-isoquinolinesulfonyl)-2-methylpiperazine is preferred.

In the case where the present compound is combined with two other preventive or therapeutic drugs for glaucoma or ocular hypertension, specific examples of the two other preventive or therapeutic drugs for glaucoma or ocular hypertension include timolol and dorzolamide, timolol and latanoprost, and timolol and travoprost.

The present compound and the other preventive or therapeutic drug for glaucoma or ocular hypertension in the invention include salts thereof. Such a salt is not particularly limited as long as it is a pharmaceutically acceptable salt, and examples of the salt include a salt with an inorganic acid, a salt with an organic acid, a quaternary ammonium salt, a salt with a halogen ion, a salt with an alkali metal, a salt with an alkaline earth metal, a metal salt, a salt with ammonia, and a salt with an organic amine. Examples of the salt with an inorganic acid include salts with hydrochloric acid, hydrobromic acid, hydroiodic acid, nitric acid, sulfuric acid, phosphoric acid or the like. Examples of the salt with an organic acid include salts with acetic acid, oxalic acid, fumaric acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, tri fluoromethanesulfonic acid, benzenesulfonic acid, p-toluenesulfonic acid, lauryl sulfate, methyl sulfate, napthalenesulfonic acid, sulfosalicylic acid or the like. Examples of the quaternary ammonium salt include salts with methyl bromide, methyl iodide or the like. Examples of the salt with a halogen ion include salts with a chloride ion, a bromide ion, an iodide ion or the like. Examples of the salt with an alkali metal include salts with lithium, sodium, potassium or the like. Examples of the salt with an alkaline earth metal include salts with calcium, magnesium or the like. Examples of the metal salt include salts with iron, zinc or the like. Examples of the salt with an organic amine include salts with triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine, N,N-bis(phenylmethyl)-1,2-ethanediamine or the like.

In addition, the present compound and the other preventive or therapeutic drug for glaucoma or ocular hypertension in the invention also include derivatives thereof such as an ester and an amide. Specific examples of the ester include esters obtained by condensation of a hydroxyl group in the other preventive or therapeutic drug for glaucoma or ocular hypertension with a carboxylic acid such as acetic acid, propionic acid, isopropionic acid, butyric acid, isobutyric acid or pivalic acid, and esters obtained by condensation of a carboxyl group in the other preventive or therapeutic drug for glaucoma or ocular hypertension with an alcohol such as methanol, ethanol, propanol or isopropyl alcohol. Specific examples of the amide include amides obtained by condensation of an amino group in the present compound and/or the other preventive or therapeutic drug for glaucoma or ocular hypertension with a carboxylic acid such as acetic acid, propionic acid, isopropionic acid, butyric acid, isobutyric acid or pivalic acid, and amides obtained by condensation of a carboxyl group in the other preventive or therapeutic drug for glaucoma or ocular hypertension with an amine such as methylamine, ethylamine, propylamine or isopropylamine.

Further, the present compound and the other preventive or therapeutic drug for glaucoma or ocular hypertension in the invention may be in the form of a hydrate or a solvate.

As the administration form, the present compound and the other preventive or therapeutic drug for glaucoma or ocular hypertension may be administered in the form of a plurality of preparations obtained by separately formulating the respective components (concomitant administration), and also, the respective components may be administered in the form of one preparation obtained by mixing the respective components (combination drug). The case of the combination drug is preferred. Further, in the case where the present compound is combined with a plurality of the other preventive or therapeutic drugs for glaucoma or ocular hypertension, the respective components may be concomitantly administered, or a combination drug obtained by mixing arbitrary components among the present compound and the other preventive or therapeutic drugs for glaucoma or ocular hypertension and the remaining component(s) may be concomitantly administered, or a combination drug obtained by mixing all of the components may be formed.

The preparation of the invention can be administered orally or parenterally. The formulation of the preparation does not require a special technique, and can be achieved using a widely used technique. Examples of the dosage form include an eye drop, an ophthalmic ointment, an injection, a tablet, a capsule, a granule and a powder, and an eye drop or an ophthalmic ointment is preferred.

In the case where the present compound and the other preventive or therapeutic drug for glaucoma or ocular hypertension are separately formulated, the respective preparations can be prepared according to a known method. For example, the preparation of the present compound can be prepared with reference to the Preparation Example described in WO 2009/113600 or WO 2010/113957. As the preparation of the other preventive or therapeutic drug for glaucoma or ocular hypertension, a preparation which has already been commercially available such as dipivefrin, brimonidine, apraclonidine, bunazosin, timolol, befunolol, carteolol, nipradilol, betaxolol, levobunolol, metipranolol, pilocarpine, dorzolamide, brinzolamide, acetazolamide, isopropyl unoprostone, latanoprost, travoprost, bimatoprost, COSOPT (registered trademark) combination ophthalmic solution, Xalacom (registered trademark) combination ophthalmic solution, or DuoTrav (registered trademark) combination ophthalmic solution, or a preparation similar thereto can also be used. The preparation of a Rho-kinase inhibitor can be prepared with reference to the Preparation Example described in the above-described WO 00/09162, WO 97/23222 or the like.

In the case where a single preparation comprising an arbitrary combination among the present compound and a preventive or therapeutic drug for glaucoma or ocular hypertension is prepared, the preparation can be carried out in accordance with a known method.

In the case where an eye drop is prepared, by adding the present compound or the other preventive or therapeutic drug for glaucoma or ocular hypertension to purified water, a buffer or the like, followed by stirring, and then, adjusting the pH of the resulting mixture with a pH adjusting agent, whereby a desired eye drop can be prepared. Further, if necessary, a widely used additive can be used in the eye drop, and examples of the additive include a tonicity agent, a buffer, a surfactant, a stabilizer and a preservative. Examples of the tonicity agent include sodium chloride and concentrated glycerin. Examples of the buffer include sodium phosphate, sodium acetate, boric acid, borax and citric acid. Examples of the surfactant include polyoxyethylene sorbitan monooleate, polyoxyl stearate and polyoxyethylene hydrogenated castor oil. Examples of the stabilizer include sodium citrate and disodium edetate. Examples of the preservative include benzalkonium chloride and paraben.

Any pH of the eye drop is permitted as long as it falls within the range that is acceptable for an ophthalmic preparation, but is preferably in the range of from 4 to 8, more preferably in the range of from 5 to 7.

In the case where an ophthalmic ointment is prepared, the preparation can be carried out using a widely used base. Examples of the base include white petrolatum and liquid paraffin.

In the case where an oral preparation such as a tablet, a capsule, a granule or a powder is prepared, the preparation can be carried out by adding an extender, a lubricant, a binder, a disintegrant, a coating agent or a film forming agent as needed. Examples of the extender include lactose, crystalline cellulose, starch and a vegetable oil. Examples of the lubricant include magnesium stearate and talc. Examples of the binder include hydroxypropyl cellulose and polyvinylpyrrolidone. Examples of the disintegrant include carboxymethyl cellulose calcium and low-substituted hydroxypropylmethyl cellulose. Examples of the coating agent include hydroxypropylmethyl cellulose, macrogol and a silicone resin. Examples of the film forming agent include a gelatin film.

The dose of the present compound and the other preventive or therapeutic drug for glaucoma or ocular hypertension can be appropriately changed depending on the dosage form, severity of symptoms, age or body weight of the patient to which the present compound or the drug is to be administered, administration route, medical opinion or the like. Hereinafter, the case of instillation administration will be mainly described as an example.

As for the dose of the present compound, in the case of an eye drop, the present compound can be generally administered once or several times per day at a daily dose of from 0.05 to 500 µg, which can be appropriately increased or decreased depending on the age or symptoms of the patient or the like. The concentration of the present compound in the eye drop is not particularly limited, but an eye drop containing the present compound at a concentration of from 0.00001 to 3 w/v %, preferably from 0.0001 to 1 w/v %, more preferably from 0.001 to 0.1 w/v %, further more preferably from 0.003 to 0.03 w/v % can be instilled once or several times per day. Incidentally, the concentration of the present compound in an eye drop may be calculated on the basis of the weight of the present compound either in a free form or in the form of a salt (hereinafter, the same shall apply). Further, in the case of an ophthalmic ointment, the present compound can be generally administered once or several times at a daily dose of generally from 0.0001 to 30 mg, preferably from 0.0003 to 10 mg, more preferably from 0.001 to 3 mg, further more preferably from 0.003 to 1 mg.

The dose of the nonselective sympathomimetic drug varies depending on the type of the drug, but it can be administered once or several times per day at a daily dose of generally from 1 to 5000 µg. More specifically, in the case of dipivefrin, a daily dose of from 2 to 3000 µg is generally used, and such a dose can be appropriately increased or decreased depending on the age or symptoms of the patient or the like. Also for other nonselective sympathomimetic drugs, the dose thereof can be determined on the basis of the same criteria. The concentration of the nonselective sympathomimetic drug in an eye drop is not particularly limited, but in the case of dipivefrin, an eye drop containing dipivefrin at a concentration of from 0.001 to 3 w/v %, preferably from 0.04 to 0.1 w/v %, more preferably 0.04 w/v % or 0.1 w/v % can be instilled once or several times per day.

The dose of the $\alpha_2$-receptor agonist varies depending on the type of the drug, but it can be administered once or several times per day at a daily dose of generally from 2 to 3000 µg. More specifically, in the case of brimonidine, a daily dose of from 2 to 1000 µg is generally used and in the case of apraclonidine, a daily dose of from 20 to 3000 µg is generally used. Such a dose can be appropriately increased or decreased depending on the age or symptoms of the patient or the like. Also for other $\alpha_2$-receptor agonists, the dose thereof can be determined on the basis of the same criteria. The concentration of the $\alpha_2$-receptor agonist in an eye drop is not particularly limited, but, in the case of brimonidine, an eye drop containing brimonidine at a concentration of from 0.01 to 5 w/v %, preferably from 0.1 to 0.5 w/v %, more preferably 0.1 w/v %, 0.15 w/v %, 0.2 w/v % or 0.5 w/v % can be instilled once or several times per day. Further, in the case of apraclonidine, an eye drop containing apraclonidine at a concentration of from 0.01 to 5 w/v %, preferably from 0.5 to 1 w/v %, more preferably 0.5 w/v % or 1 w/v % can be instilled once or several times per day.

The dose of the $\alpha_1$-receptor antagonist varies depending on the type of the drug, but it can be administered once or several times per day at a daily dose of generally from 1 to 5000 µg. More specifically, in the case of bunazosin, a daily dose of from 2 to 3000 µg is generally used, and such a dose can be appropriately increased or decreased depending on the age or symptoms of the patient or the like. Also for other $\alpha_1$-receptor antagonists, the dose thereof can be determined on the basis of the same criteria. The concentration of the $\alpha_1$-receptor antagonist in an eye drop is not particularly limited, but, in the case of bunazosin, an eye drop containing bunazosin at a concentration of from 0.001 to 0.3 w/v %, preferably from 0.003 to 0.03 w/v %, more preferably 0.01 w/v % can be instilled once or several times per day.

The dose of the $\beta$-receptor antagonist varies depending on the type of the drug, but it can be administered once or several times per day at a daily dose of generally from 5 to 5000 µg. More specifically, in the case of timolol, a daily dose of from 5 to 1500 µg is generally used, in the case of befunolol, a daily dose of from 10 to 2000 µg is generally used, in the case of carteolol, a daily dose of from 10 to 5000 µg is generally used, in the case of nipradilol, a daily dose of from 10 to 1250 µg is generally used, in the case of betaxolol, a daily dose of from 50 to 1000 µg is generally used, in the case of levobunolol, a daily dose of from 5 to 5000 µg is generally used, and in the case of metipranolol, a daily dose of from 5 to 5000 µg is generally used. Such a dose can be appropriately increased or decreased depending on the age or symptoms of the patient or the like. Also for other $\beta$-receptor antagonists, the dose thereof can be determined on the basis of the same criteria. The concentration of the $\beta$-receptor antagonist in an eye drop is not particularly limited, but, in the case of timolol, an eye drop containing timolol at a concentration of from 0.01 to 5 w/v %, preferably from 0.1 to 0.5 w/v %, more preferably 0.1 w/v %, 0.25 w/v % or 0.5 w/v % can be instilled once or several times per day. Further, in the case of befunolol, an eye drop containing befunolol at a concentration of from 0.01 to 5 w/v %, preferably from 0.25 to 1 w/v %, more preferably 0.25 w/v %, 0.5 w/v % or 1 w/v % can be instilled once or several times per day. In the case of carteolol, an eye drop containing carteolol at a concentration of from 0.01 to 5 w/v %, preferably from 1 to 2 w/v %, more preferably 1 w/v % or 2 w/v % can be instilled once or several times per day. In the case of nipradilol, an eye drop containing nipradilol at a concentration of from 0.01 to 5 w/v %, preferably 0.25 w/v % can be instilled once or several times per day. In the case of betaxolol, an eye drop containing betaxolol at a concentration of from 0.01 to 5 w/v %, preferably from 0.25 to 0.5 w/v %, more preferably 0.25 w/v % or 0.5 w/v % can be instilled once or several times per day. In the case of levobunolol, an eye drop containing levobunolol at a concentration of from 0.01 to 5 w/v %, preferably from 0.25 to 0.5 w/v %, more preferably 0.25 w/v % or 0.5 w/v % can be instilled once or several times per day. In the case of metipranolol, an eye drop containing metipranolol at a concentration of from 0.01 to 5 w/v %, preferably 0.3 w/v % can be instilled once or several times per day.

The dose of the parasympathomimetic drug varies depending on the type of the drug, but it can be administered once or several times per day at a daily dose of generally from 5 to 300000 µg. More specifically, in the case of pilocarpine, a daily dose of from 5 to 200000 µg is generally used, and such a dose can be appropriately increased or decreased depending on the age or symptoms of the patient or the like. Also for other parasympathomimetic drugs, the dose thereof can be determined on the basis of the same criteria. The concentration of the parasympathomimetic drug in an eye drop is not particularly limited, but, in the case of pilocarpine, an eye drop containing pilocarpine at a concentration of from 0.01 to 20 w/v %, preferably from 0.1 to 5 w/v %, more preferably 0.5 w/v %, 1 w/v %, 2 w/v %, 3 w/v % or 4 w/v % can be instilled once or several times per day.

The dose of the carbonic anhydrase inhibitor varies depending on the type of the drug, but it can be administered once or several times per day at a daily dose of generally from 10 to 10000 µg. More specifically, in the case of dorzolamide, a daily dose of from 10 to 10000 µg is generally used and in the case of brinzolamide, a daily dose of from 20 to 5000 µg is generally used. Such a dose can be appropriately increased or decreased depending on the age or symptoms of the patient or the like. Also for other carbonic anhydrase inhibitors, the dose thereof can be determined on the basis of the same criteria. The concentration of the carbonic anhydrase inhibitor in an eye drop is not particularly limited, but, in the case of dorzolamide, an eye drop containing dorzolamide at a concentration of from 0.01 to 5 w/v %, preferably from 0.5 to 2 w/v %, more preferably 0.5 w/v %, 1 w/v % or 2 w/v % can be instilled once or several times per day. Further, in the case of brinzolamide, an eye drop containing brinzolamide at a concentration of from 0.01 to 5 w/v %, preferably from 0.1 to 2 w/v %, more preferably 1 w/v % can be instilled once or several times per day. Further, in the case of acetazolamide, an eye drop containing acetazolamide at a concentration of from 0.01 to 5 w/v %, preferably from 1 to 5 w/v % can be used. Incidentally, in the case where acetazolamide is orally administered, a daily dose of from 250 to 1000 mg can be used.

The dose of the prostaglandin varies depending on the type of the drug, but it can be administered once or several times per day at a daily dose of generally from 0.1 to 1000 µg. More specifically, in the case of latanoprost, a daily dose of from 1 to 5 µg is generally used, in the case of isopropyl unoprostone, a daily dose of from 30 to 300 µg is generally used, in the case of bimatoprost, a daily dose of from 2 to 30 µg is generally used, and in the case of travoprost, a daily dose of from 0.5 to 5 µg is generally used. Such a dose can be appropriately increased or decreased depending on the age or symptoms of the patient or the like. Also for other prostaglandins, the dose thereof can be determined on the basis of the same criteria. The concentration of the prostaglandin in an eye drop is not particularly limited, but, in the case of latanoprost, an eye drop containing latanoprost at a concentration of from 0.0001 to 5 w/v %, preferably from 0.0005 to 1 w/v %, more preferably 0.001 to 0.1 w/v %, further more preferably 0.005 w/v % can be instilled once or several times per day. In the case of isopropyl unoprostone, an eye drop containing isopropyl unoprostone at a concentration of from 0.001 to 5 w/v %, preferably from 0.01 to 1 w/v %, more preferably 0.12 to 0.15 w/v %, further more preferably 0.12 w/v % or 0.15 w/v % can be instilled once or several times per day. In the case of bimatoprost, an eye drop containing bimatoprost at a concentration of from 0.0001 to 5 w/v %, preferably from 0.001 to 1 w/v %, more preferably 0.01 to 0.03 w/v %, further more preferably 0.01 w/v % or 0.03 w/v % can be instilled once or several times per day. In the case of travoprost, an eye drop containing travoprost at a concentration of from 0.0001 to 5 w/v %, preferably 0.001 to 1 w/v % more preferably 0.004 w/v % can be instilled once or several times per day.

The dose of the Rho-kinase inhibitor varies depending on the type of the drug, but it can be administered once or several times per day at a daily dose of generally from 0.025 to 10000 µg, and such a dose can be appropriately increased or decreased depending on the age or symptoms of the patient or the like. The concentration of the Rho-kinase inhibitor in an eye drop is not particularly limited, but an eye drop containing the Rho-kinase inhibitor at a concentration of from 0.0001 to 5 w/v %, preferably from 0.001 to 1 w/v % can be instilled once or several times per day.

Such a dose is applied when the present compound and the other preventive or therapeutic drug for glaucoma or ocular hypertension are concomitantly administered. In the case where a combination drug comprising an arbitrary combination of the present compound and the other preventive or therapeutic drugs for glaucoma or ocular hypertension is administered, a preparation in which the mixing ratios are appropriately selected so that the daily dose of each component falls within the above-described dose range is prepared, and the thus prepared combination preparation can be administered once or several times per day.

Hereinafter, preparation examples and pharmacological tests will be shown, but these are for understanding the invention better, and are not meant to limit the scope of the invention.

PREPARATION EXAMPLES

Hereinafter, specific preparation examples of an eye drop and an ophthalmic ointment containing the present compound and the other preventive or therapeutic drug for glaucoma or ocular hypertension according to the invention will be shown.

Preparation Example 1

| Eye Drop (in 100 mL) | |
| --- | --- |
| Present compound | 0.01 g |
| Dipivefrin hydrochloride | 0.04 g |
| Sodium dihydrogen phosphate | 0.15 g |
| Glycerin | q.s. |
| Polyoxyl 35 castor oil | 1.7 g |
| Disodium edetate | 0.05 g |
| Benzalkonium chloride | 0.005 g |
| Diluted hydrochloric acid | q.s. |
| Sodium hydroxide | q.s. |
| Purified water | q.s. |

Preparation Example 2

| Eye Drop (in 100 mL) | |
| --- | --- |
| Present compound | 0.01 g |
| Timolol maleate | 0.25 g |
| Sodium dihydrogen phosphate | 0.15 g |
| Glycerin | q.s. |
| Polyoxyl 35 castor oil | 1.7 g |
| Disodium edetate | 0.05 g |
| Benzalkonium chloride | 0.005 g |
| Diluted hydrochloric acid | q.s. |
| Sodium hydroxide | q.s. |
| Purified water | q.s. |

Preparation Example 3

| Eye Drop (in 100 mL) | |
| --- | --- |
| Present compound | 0.01 g |
| Timolol maleate | 0.5 g |
| Sodium dihydrogen phosphate | 0.15 g |
| Glycerin | q.s. |
| Polyoxyl 35 castor oil | 1.7 g |
| Disodium edetate | 0.05 g |
| Benzalkonium chloride | 0.005 g |
| Diluted hydrochloric acid | q.s. |
| Sodium hydroxide | q.s. |
| Purified water | q.s. |

Preparation Example 4

| Eye Drop (in 100 mL) | |
| --- | --- |
| Present compound | 0.01 g |
| Dorzolamide hydrochloride | 0.5 g |
| Sodium dihydrogen phosphate | 0.15 g |
| Glycerin | q.s. |
| Polyoxyl 35 castor oil | 1.7 g |
| Disodium edetate | 0.05 g |
| Benzalkonium chloride | 0.005 g |
| Diluted hydrochloric acid | q.s. |
| Sodium hydroxide | q.s. |
| Purified water | q.s. |

Preparation Example 5

| Eye Drop (in 100 mL) | |
| --- | --- |
| Present compound | 0.01 g |
| Brinzolamide | 1 g |
| Sodium dihydrogen phosphate | 0.15 g |
| Glycerin | q.s. |
| Polyoxyl 35 castor oil | 1.7 g |
| Disodium edetate | 0.05 g |
| Benzalkonium chloride | 0.005 g |
| Diluted hydrochloric acid | q.s. |
| Sodium hydroxide | q.s. |
| Purified water | q.s. |

Preparation Example 6

| Eye Drop (in 100 mL) | |
| --- | --- |
| Present compound | 0.01 g |
| Dorzolamide hydrochloride | 1 g |
| Timolol maleate | 0.5 g |
| Sodium dihydrogen phosphate | 0.15 g |
| Glycerin | q.s. |
| Polyoxyl 35 castor oil | 1.7 g |
| Disodium edetate | 0.05 g |
| Benzalkonium chloride | 0.005 g |
| Diluted hydrochloric acid | q.s. |
| Sodium hydroxide | q.s. |
| Purified water | q.s. |

Preparation Example 7

| Eye Drop (in 100 mL) | |
| --- | --- |
| Present compound | 0.01 g |
| Isopropyl unoprostone | 0.12 g |
| Sodium dihydrogen phosphate | 0.15 g |
| Glycerin | q.s. |
| Polyoxyl 35 castor oil | 1.7 g |
| Disodium edetate | 0.05 g |
| Benzalkonium chloride | 0.005 g |
| Diluted hydrochloric acid | q.s. |
| Sodium hydroxide | q.s. |
| Purified water | q.s. |

Preparation Example 8

| Eye Drop (in 100 mL) | |
| --- | --- |
| Present compound | 0.01 g |
| Latanoprost | 0.005 g |
| Sodium dihydrogen phosphate | 0.15 g |
| Glycerin | q.s. |
| Polyoxyl 35 castor oil | 1.7 g |
| Disodium edetate | 0.05 g |
| Benzalkonium chloride | 0.005 g |
| Diluted hydrochloric acid | q.s. |
| Sodium hydroxide | q.s. |
| Purified water | q.s. |

Preparation Example 9

| Eye Drop (in 100 mL) | |
| --- | --- |
| Present compound | 0.01 g |
| Bimatoprost | 0.01 g |
| Sodium dihydrogen phosphate | 0.15 g |
| Glycerin | q.s. |
| Polyoxyl 35 castor oil | 1.7 g |
| Disodium edetate | 0.05 g |
| Benzalkonium chloride | 0.005 g |
| Diluted hydrochloric acid | q.s. |
| Sodium hydroxide | q.s. |
| Purified water | q.s. |

Preparation Example 10

| Eye Drop (in 100 mL) | |
| --- | --- |
| Present compound | 0.01 g |
| Travoprost | 0.004 g |
| Sodium dihydrogen phosphate | 0.15 g |
| Glycerin | q.s. |
| Polyoxyl 35 castor oil | 1.7 g |
| Disodium edetate | 0.05 g |
| Benzalkonium chloride | 0.005 g |
| Diluted hydrochloric acid | q.s. |
| Sodium hydroxide | q.s. |
| Purified water | q.s. |

Preparation Example 11

| Eye Drop (in 100 mL) | |
| --- | --- |
| Present compound | 0.01 g |
| Latanoprost | 0.005 g |
| Timolol maleate | 0.5 g |
| Sodium dihydrogen phosphate | 0.15 g |
| Glycerin | q.s. |
| Polyoxyl 35 castor oil | 1.7 g |
| Disodium edetate | 0.05 g |
| Benzalkonium chloride | 0.005 g |
| Diluted hydrochloric acid | q.s. |
| Sodium hydroxide | q.s. |
| Purified water | q.s. |

Preparation Example 12

| Eye Drop (in 100 mL) | |
| --- | --- |
| Present compound | 0.01 g |
| Brimonidine tartrate | 0.1 g |
| Sodium dihydrogen phosphate | 0.15 g |
| Glycerin | q.s. |
| Polyoxyl 35 castor oil | 1.7 g |
| Disodium edetate | 0.05 g |
| Benzalkonium chloride | 0.005 g |
| Diluted hydrochloric acid | q.s. |
| Sodium hydroxide | q.s. |
| Purified water | q.s. |

Preparation Example 13

| Eye Drop (in 100 mL) | |
| --- | --- |
| Present compound | 0.01 g |
| Brimonidine tartrate | 0.2 g |
| Sodium dihydrogen phosphate | 0.15 g |
| Glycerin | q.s. |
| Polyoxyl 35 castor oil | 1.7 g |
| Disodium edetate | 0.05 g |
| Benzalkonium chloride | 0.005 g |
| Diluted hydrochloric acid | q.s. |
| Sodium hydroxide | q.s. |
| Purified water | q.s. |

Preparation Example 14

| Eye Drop (in 100 mL) | |
| --- | --- |
| Present compound | 0.01 g |
| Bunazosin hydrochloride | 0.01 g |
| Sodium dihydrogen phosphate | 0.15 g |
| Glycerin | q.s. |
| Polyoxyl 35 castor oil | 1.7 g |
| Disodium edetate | 0.05 g |
| Benzalkonium chloride | 0.005 g |
| Diluted hydrochloric acid | q.s. |
| Sodium hydroxide | q.s. |
| Purified water | q.s. |

Preparation Example 15

| Eye Drop (in 100 mL) | |
| --- | --- |
| Present compound | 0.01 g |
| Pilocarpine hydrochloride | 0.5 g |
| Sodium dihydrogen phosphate | 0.15 g |
| Glycerin | q.s. |
| Polyoxyl 35 castor oil | 1.7 g |
| Disodium edetate | 0.05 g |
| Benzalkonium chloride | 0.005 g |
| Diluted hydrochloric acid | q.s. |
| Sodium hydroxide | q.s. |
| Purified water | q.s. |

Preparation Example 16

| Ophthalmic Ointment (in 100 g) | |
| --- | --- |
| Present compound | 0.01 g |
| Timolol maleate | 0.5 g |
| Liquid paraffin | 10.0 g |
| White petrolatum | q.s. |

Preparation Example 17

| Ophthalmic Ointment (in 100 g) | |
| --- | --- |
| Present compound | 0.01 g |
| Isopropyl unoprostone | 0.12 g |

-continued

| Ophthalmic Ointment (in 100 g) | |
|---|---|
| Liquid paraffin | 10.0 g |
| White petrolatum | q.s. |

Preparation Example 18

| Ophthalmic Ointment (in 100 g) | |
|---|---|
| Present compound | 0.01 g |
| Latanoprost | 0.005 g |
| Liquid paraffin | 10.0 g |
| White petrolatum | q.s. |

In the above formulations, by changing the amount of the present compound to 0.001 g, 0.003 g, 0.03 g, 0.1 g, etc., and by changing the type and amount of the other preventive or therapeutic drug for glaucoma or ocular hypertension and/or the additive, an eye drop or an ophthalmic ointment having a desired combination and a desired concentration can be prepared.

Pharmacological Tests

Example 1

In order to study the usefulness of the combination of the present compound with a β-receptor antagonist, an intraocular pressure lowering effect when the present compound and timolol were concomitantly administered to experimental animals (rabbits with normal intraocular pressure) was examined.

(Preparation of Test Compound Solution)
(1) Preparation of Base
To 1.7 g of polyoxyl 35 castor oil, 10 mL of a 0.5% disodium edetate/10% glycerin solution, 1 mL of a 1% benzalkonium chloride solution, 30 mL of purified water, and 50 mL of a 2% boric acid/0.2% sorbic acid solution were added and dissolved. After confirming that a solution was obtained, an appropriate amount of a sodium hydroxide solution or diluted hydrochloric acid was added thereto to adjust the pH of the preparation to around 6.5. Then, an appropriate amount of purified water was added thereto to make the total volume 100 mL.

(2) Preparation of Present Compound Solution
To 0.8 g of polyoxyl 35 castor oil, 0.001 g of the present compound was added, and then, 10 mL of a 0.5% disodium edetate/10% glycerin solution, 1 mL of a 1% benzalkonium chloride solution, 30 mL of purified water, and 50 mL of a 2% boric acid/0.2% sorbic acid solution were added thereto and dissolved. After confirming that a solution was obtained, an appropriate amount of a sodium hydroxide solution or diluted hydrochloric acid was added thereto to adjust the pH of the preparation to around 6.5. Then, an appropriate amount of purified water was added thereto to make the total volume 100 mL.

(3) Preparation of Physiological Saline
Commercially available physiological saline (trade name: Otsuka Normal Saline, obtained from Otsuka Pharmaceutical Factory, Inc.) was used as such.

(4) Preparation of Timolol Solution
A commercially available timolol eye drop was used as such.

(Test Method)
An intraocular pressure lowering effect when the present compound and timolol were concomitantly administered was examined. As comparison subjects, intraocular pressure lowering effects when the present compound or timolol was administered singly were also examined. As a control, the base and physiological saline were administered.

(Drugs and Animals Used in Test)
Present compound solution: a 0.001 w/v % present compound solution (instillation amount: 50 μL)

Timolol solution: a timolol eye drop (trade name: Timoptol (registered trademark) eye drop (0.5%), in which the active ingredient is timolol maleate having an equivalent timolol content of 0.5 w/v %; instillation amount: 50 μL).

Experimental animal: Japanese white rabbit (strain: JW, sex: male, six rabbits per group)

(Administration Method and Measurement Method)
[1] Concomitant Administration of Present Compound and Timolol (1) One drop of a 0.4% oxybuprocaine hydrochloride eye drop (trade name: Benoxil (registered trademark) eye drop (0.4%)) was instilled into both eyes of each experimental animal to effect local anesthesia.

(2) Intraocular pressure was measured immediately before administering the test compound solution, and the measured intraocular pressure was defined as initial intraocular pressure.

(3) The present compound solution was instilled into one eye of each experimental animal (the other eye was not treated). A few minutes later, the timolol solution was instilled into the same eye.

(4) At 2, 4 and 6 hours after instilling the present compound solution, one drop of the 0.4% oxybuprocaine hydrochloride eye drop was instilled into the eyes for which intraocular pressure was to be measured to effect local anesthesia, and then, intraocular pressure was measured. The intraocular pressure was measured in triplicate for each eye to obtain an average of three measurements, which is shown as the result.

[2] Single Administration of Present Compound
A test was carried out in the same manner as in the above-described concomitant administration test except that physiological saline was used in place of the timolol solution.

[3] Single Administration of Timolol
A test was carried out in the same manner as in the above-described concomitant administration test except that the base was used in place of the present compound solution.

[4] Control
A test was carried out in the same manner as in the above-described concomitant administration test except that the base was used in place of the present compound solution and physiological saline was used in place of the timolol solution.

(Results and Discussion)
An intraocular pressure lowering degree (change relative to the average of the control group) at 4 hours after instillation for each administration group is shown in Table 1. The intraocular pressure lowering degree (change relative to the average of the control group) is expressed as an average of differences for 6 rabbits in each group between an average of intraocular pressure change (ΔIOP) from the initial intraocular pressure of the control group and ΔIOP of each individual.

TABLE 1

| Administration group | Intraocular pressure lowering degree (change relative to average of control group) at 4 hours after instillation (mmHg) |
|---|---|
| Control group | 0.0 |
| Present compound single administration group | 1.6 |
| Timolol single administration group | 2.3 |
| Present compound and timolol concomitant administration group | 6.4 |

As apparent from Table 1, the intraocular pressure lowering degree (change relative to the average of the control group) at 4 hours after instillation of the present compound and timolol concomitant administration group was larger than that of each drug single administration group, i.e., the present compound administration group or the timolol administration group, and moreover, the intraocular pressure lowering degree was larger than the sum of the intraocular pressure lowering degrees (changes relative to the average of the control group) at 4 hours after instillation caused by the single administration of each drug. Accordingly, the effect of the combination of the present compound with timolol was synergistic.

From the above results, it was found that by combining the present compound with a β-receptor antagonist, a synergistic intraocular pressure lowering effect is obtained.

Example 2

In order to study the usefulness of a combination of the present compound with a prostaglandin, an intraocular pressure lowering effect when the present compound and latanoprost were concomitantly administered to experimental animals (monkeys with normal intraocular pressure) was examined.

(Preparation of Test Compound Solution)
(1) Preparation of Base
To 1.7 g of polyoxyl 35 castor oil, 10 mL of a 0.5% disodium edetate/10% glycerin solution, 1 mL of a 1% benzalkonium chloride solution, 30 mL of purified water, and 50 mL of a 2% boric acid/0.2% sorbic acid solution were added and dissolved. After confirming that a solution was obtained, an appropriate amount of a sodium hydroxide solution or diluted hydrochloric acid was added thereto to adjust the pH of the preparation to around 6.5. Then, an appropriate amount of purified water was added thereto to make the total volume 100 mL.

(2) Preparation of Present Compound Solution
To 0.8 g of polyoxyl 35 castor oil, 0.0006 g of the present compound was added, and then, 10 mL of a 0.5% disodium edetate/10% glycerin solution, 1 mL of a 1% benzalkonium chloride solution, 30 mL of purified water, and 50 mL of a 2% boric acid/0.2% sorbic acid solution were added thereto and dissolved. After confirming that a solution was obtained, an appropriate amount of a sodium hydroxide solution or diluted hydrochloric acid was added thereto to adjust the pH of the preparation to around 6.5. Then, an appropriate amount of purified water was added thereto to make the total volume 100 mL.

(3) Preparation of Physiological Saline
Commercially available physiological saline (trade name: Otsuka Normal Saline, obtained from Otsuka Pharmaceutical Factory, Inc.) was used as such.

(4) Preparation of Latanoprost Solution
A commercially available latanoprost eye drop was used as such.

(Test Method)
An intraocular pressure lowering effect when the present compound and latanoprost were concomitantly administered was examined. As comparison subjects, intraocular pressure lowering effects when the present compound or latanoprost was administered singly were also examined. As a control, the base and physiological saline were administered.

(Drugs and Animals Used in Test)
Present compound solution: a 0.0006 w/v % present compound solution (instillation amount: 20 μL)
Latanoprost solution: a latanoprost eye drop (trade name: Xalatan (registered trademark) eye drop (0.005%), (instillation amount: 20 μL))
Experimental animal: Cynomolgus monkey (sex: male, six monkeys per group)

(Administration Method and Measurement Method)
[1] Concomitant Administration of Present Compound and Latanoprost
(1) One drop of a 0.4% oxybuprocaine hydrochloride eye drop (trade name: Benoxil (registered trademark) eye drop (0.4%)) was instilled into both eyes of each experimental animal to effect local anesthesia.
(2) Intraocular pressure was measured immediately before administering the test compound solution, and the measured intraocular pressure was defined as initial intraocular pressure.
(3) The present compound solution was instilled into one eye of each experimental animal (the other eye was not treated). A few minutes later, the latanoprost solution was instilled into the same eye.
(4) At 2, 4, 6 and 8 hours after instilling the present compound solution, one drop of the 0.4% oxybuprocaine hydrochloride eye drop was instilled into the eyes for which intraocular pressure was to be measured to effect local anesthesia, and then, intraocular pressure was measured. The intraocular pressure was measured in triplicate for each eye to obtain an average of three measurements, which is shown as the result.

[2] Single Administration of Present Compound
A test was carried out in the same manner as in the above-described concomitant administration test except that physiological saline was used in place of the latanoprost solution.

[3] Single Administration of Latanoprost
A test was carried out in the same manner as in the above-described concomitant administration test except that the base was used in place of the present compound solution.

[4] Control
A test was carried out in the same manner as in the above-described concomitant administration test except that the base was used in place of the present compound solution and physiological saline was used in place of the latanoprost solution.

(Results and Discussion)
An intraocular pressure lowering degree (change relative to the average of the control group) at 8 hours after instillation for each administration group is shown in Table 2. The intraocular pressure lowering degree (change relative to the average of the control group) is expressed as an average of differences for 6 monkeys in each group between an average of intraocular pressure change (ΔIOP) from the initial intraocular pressure of the control group and ΔIOP of each individual.

TABLE 2

| Administration group | Intraocular pressure lowering degree (change relative to average of control group) at 8 hours after instillation (mmHg) |
|---|---|
| Control group | 0.0 |
| Present compound single administration group | 1.6 |
| Latanoprost single administration group | 1.5 |
| Present compound and latanoprost concomitant administration group | 3.3 |

As apparent from Table 2, the intraocular pressure lowering degrees at 8 hours after instillation of the present compound and latanoprost concomitant administration group was larger than that of each drug single administration group, i.e., the present compound administration group or the latanoprost administration group, and moreover, was larger than the sum of the intraocular pressure lowering degrees (changes relative to the average of the control group) at 8 hours after instillation caused by the single administration of each drug. Accordingly, the effect of the combination of the present compound with latanoprost was synergistic.

From the above results, it was found that by combining the present compound with a prostaglandin, a synergistic intraocular pressure lowering effect is obtained.

Example 3

In order to study the usefulness of a combination of the present compound with an $\alpha_2$-receptor agonist, an intraocular pressure lowering effect when the present compound and brimonidine were concomitantly administered to experimental animals (monkeys with normal intraocular pressure) was examined.

(Preparation of Test Compound Solution)
(1) Preparation of Base

To 1.7 g of polyoxyl 35 castor oil, 10 mL of a 0.5% disodium edetate/10% glycerin solution, 1 mL of a 1% benzalkonium chloride solution, 30 mL of purified water, and 50 mL of a 2% boric acid/0.2% sorbic acid solution were added and dissolved. After confirming that a solution was obtained, an appropriate amount of a sodium hydroxide solution or diluted hydrochloric acid was added thereto to adjust the pH of the preparation to around 6.5. Then, an appropriate amount of purified water was added thereto to make the total volume 100 mL.

(2) Preparation of Present Compound Solution

To 0.8 g of polyoxyl 35 castor oil, 0.0006 g of the present compound was added, and then, 10 mL of a 0.5% disodium edetate/10% glycerin solution, 1 mL of a 1% benzalkonium chloride solution, 30 mL of purified water, and 50 mL of a 2% boric acid/0.2% sorbic acid solution were added thereto and dissolved. After confirming that a solution was obtained, an appropriate amount of a sodium hydroxide solution or diluted hydrochloric acid was added thereto to adjust the pH of the preparation to around 6.5. Then, an appropriate amount of purified water was added thereto to make the total volume 100 mL.

(3) Preparation of Physiological Saline

Commercially available physiological saline (trade name: Otsuka Normal Saline, obtained from Otsuka Pharmaceutical Factory, Inc.) was used as such.

(4) Preparation of Brimonidine Solution

A commercially available brimonidine eye drop was used as such.

(Test Method)

An intraocular pressure lowering effect when the present compound and brimonidine were concomitantly administered was examined. As comparison subjects, intraocular pressure lowering effects when the present compound or brimonidine was administered singly were also examined. As a control, the base and physiological saline were administered.

(Drugs and Animals Used in Test)

Present compound solution: a 0.0006 w/v % present compound solution (instillation amount: 20 µL)

Brimonidine solution: a brimonidine eye drop (trade name: ALPHAGAN (registered trademark) P (0.15%), (instillation amount: 20 µL))

Experimental animal: Cynomolgus monkey (sex: male, six monkeys per group)

(Administration Method and Measurement Method)

[1] Concomitant Administration of Present Compound and Brimonidine (1) One drop of a 0.4% oxybuprocaine hydrochloride eye drop (trade name: Benoxil (registered trademark) eye drop (0.4%)) was instilled into both eyes of each experimental animal to effect local anesthesia.

(2) Intraocular pressure was measured immediately before administering the test compound solution, and the measured intraocular pressure was defined as initial intraocular pressure.

(3) The present compound solution was instilled into one eye of each experimental animal (the other eye was not treated). A few minutes later, the brimonidine solution was instilled into the same eye.

(4) At 2, 4, 6 and 8 hours after instilling the present compound solution, one drop of the 0.4% oxybuprocaine hydrochloride eye drop was instilled into the eyes for which intraocular pressure was to be measured to effect local anesthesia, and then, intraocular pressure was measured. The intraocular pressure was measured in triplicate for each eye to obtain an average of three measurements, which is shown as the result.

[2] Single Administration of Present Compound

A test was carried out in the same manner as in the above-described concomitant administration test except that physiological saline was used in place of the brimonidine solution.

[3] Single Administration of Brimonidine

A test was carried out in the same manner as in the above-described concomitant administration test except that the base was used in place of the present compound solution.

[4] Control

A test was carried out in the same manner as in the above-described concomitant administration test except that the base was used in place of the present compound solution and physiological saline was used in place of the brimonidine solution.

(Results and Discussion)

An intraocular pressure lowering degree (change relative to the average of the control group) at 2 hours after instillation for each administration group is shown in Table 3. The intraocular pressure lowering degree (change relative to the average of the control group) is expressed as an average of differences for 6 monkeys in each group between an average of intraocular pressure change ($\Delta$IOP) from the initial intraocular pressure of the control group and $\Delta$IOP of each individual.

TABLE 3

| Administration group | Intraocular pressure lowering degree (change relative to average of control group) at 2 hours after instillation (mmHg) |
| --- | --- |
| Control group | 0.0 |
| Present compound single administration group | 2.6 |
| Brimonidine single administration group | 1.8 |
| Present compound and brimonidine concomitant administration group | 5.3 |

As apparent from Table 3, the intraocular pressure lowering degrees at 2 hours after instillation of the present compound and brimonidine concomitant administration group was larger than that of each drug single administration group, i.e., the present compound administration group or the brimonidine administration group, and moreover, was larger than the sum of the intraocular pressure lowering degrees (changes relative to the average of the control group) at 2 hours after instillation caused by the single administration of each drug. Accordingly, the effect of the combination of the present compound with brimonidine was synergistic.

From the above results, it was found that by combining the present compound with an $\alpha_2$-receptor agonist, a synergistic intraocular pressure lowering effect is obtained.

Example 4

In order to study the usefulness of a combination of the present compound with a carbonic anhydrase inhibitor, an intraocular pressure lowering effect when the present compound and brinzolamide were concomitantly administered to experimental animals (monkeys with normal intraocular pressure) was examined.

(Preparation of Test Compound Solution)
(1) Preparation of Base

To 1.7 g of polyoxyl 35 castor oil, 10 mL of a 0.5% disodium edetate/10% glycerin solution, 1 mL of a 1% benzalkonium chloride solution, 30 mL of purified water, and 50 mL of a 2% boric acid/0.2% sorbic acid solution were added and dissolved. After confirming that a solution was obtained, an appropriate amount of a sodium hydroxide solution or diluted hydrochloric acid was added thereto to adjust the pH of the preparation to around 6.5. Then, an appropriate amount of purified water was added thereto to make the total volume 100 mL.

(2) Preparation of Present Compound Solution

To 0.8 g of polyoxyl 35 castor oil, 0.0006 g of the present compound was added, and then, 10 mL of a 0.5% disodium edetate/10% glycerin solution, 1 mL of a 1% benzalkonium chloride solution, 30 mL of purified water, and 50 mL of a 2% boric acid/0.2% sorbic acid solution were added thereto and dissolved. After confirming that a solution was obtained, an appropriate amount of a sodium hydroxide solution or diluted hydrochloric acid was added thereto to adjust the pH of the preparation to around 6.5. Then, an appropriate amount of purified water was added thereto to make the total volume 100 mL.

(3) Preparation of Physiological Saline

Commercially available physiological saline (trade name: Otsuka Normal Saline, obtained from Otsuka Pharmaceutical Factory, Inc.) was used as such.

(4) Preparation of brinzolamide suspension

A commercially available brinzolamide eye drop was used as such.

(Test Method)

An intraocular pressure lowering effect when the present compound and brinzolamide were concomitantly administered was examined. As comparison subjects, intraocular pressure lowering effects when the present compound or brinzolamide was administered singly were also examined. As a control, the base and physiological saline were administered.

(Drugs and Animals Used in Test)

Present compound solution: a 0.0006 w/v % present compound solution (instillation amount: 20 μL)

Brinzolamide suspension: a brinzolamide ophthalmic suspension (trade name: Azopt (registered trademark) Ophthalmic Suspension (1%), (instillation amount: 20 μL))

Experimental animal: Cynomolgus monkey (sex: male, five or six monkeys per group)

(Administration Method and Measurement Method)

[1] Concomitant Administration of Present Compound and Brinzolamide (1) One drop of a 0.4% oxybuprocaine hydrochloride eye drop (trade name: Benoxil (registered trademark) eye drop (0.4%)) was instilled into both eyes of each experimental animal to effect local anesthesia.

(2) Intraocular pressure was measured immediately before administering the test compound solution, and the measured intraocular pressure was defined as initial intraocular pressure.

(3) The present compound solution was instilled into one eye of each experimental animal (the other eye was not treated). A few minutes later, the brinzolamide suspension was instilled into the same eye.

(4) At 2, 4, 6 and 8 hours after instilling the present compound solution, one drop of the 0.4% oxybuprocaine hydrochloride eye drop was instilled into the eyes for which intraocular pressure was to be measured to effect local anesthesia, and then, intraocular pressure was measured. The intraocular pressure was measured in triplicate for each eye to obtain an average of three measurements, which is shown as the result.

[2] Single Administration of Present Compound

A test was carried out in the same manner as in the above-described concomitant administration test except that physiological saline was used in place of the brinzolamide suspension.

[3] Single Administration of Brinzolamide

A test was carried out in the same manner as in the above-described concomitant administration test except that the base was used in place of the present compound solution.

[4] Control

A test was carried out in the same manner as in the above-described concomitant administration test except that the base was used in place of the present compound solution and physiological saline was used in place of the brinzolamide suspension.

(Results and Discussion)

An intraocular pressure lowering degree (change relative to the average of the control group) at 4 hours after instillation for each administration group is shown in Table 4. The intraocular pressure lowering degree (change relative to the average of the control group) is expressed as an average of differences for 5 or 6 monkeys in each group between an average of intraocular pressure change (ΔIOP) from the initial intraocular pressure of the control group and ΔIOP of each individual.

TABLE 4

| Administration group | Intraocular pressure lowering degree (change relative to average of control group) at 4 hours after instillation (mmHg) |
|---|---|
| Control group | 0.0 |
| Present compound single administration group | 2.5 |
| Brinzolamide single administration group | 1.6 |
| Present compound and brinzolamide concomitant administration group | 3.2 |

As apparent from Table 4, the intraocular pressure lowering degree at 4 hours after instillation of the present compound and brinzolamide concomitant administration group was larger than that of each drug single administration group, i.e., the present compound administration group or the brinzolamide administration group.

From the above results, it was found that by combining the present compound with a carbonic anhydrase inhibitor, a potent intraocular pressure lowering effect is obtained.

What is claimed is:

1. A composition for treating glaucoma or ocular hypertension comprising 0.001 to 0.1 w/v % of isopropyl (6-{[4-(pyrazol-1-yl)benzyl](pyridin-3-ylsulfonyl) aminomethyl}pyridin-2-ylamino)acetate and 0.1 to 0.5 w/v % of timolol, in a combined pharmaceutically effective amount, wherein the isopropyl (6-{[4-(pyrazol-1-yl)benzyl](pyridin-3-ylsulfonyl)aminomethyl}pyridin-2-ylamino)acetate may be in the form of a salt thereof, and the timolol may be in the form of a salt thereof.

2. The composition according to claim 1, wherein the composition is obtained by mixing isopropyl (6-{[4-(pyrazol-1-yl)benzyl](pyridin-3-ylsulfonyl) aminomethyl}pyridin-2-ylamino)acetate or a salt thereof and timolol or a salt thereof.

3. The composition according to claim 1, wherein the composition is obtained by providing a separate preparation for each of isopropyl (6-{[4-(pyrazol-1-yl)benzyl](pyridin-3-ylsulfonyl)aminomethyl}pyridin-2-ylamino)acetate or a salt thereof and timolol or a salt thereof, for a concomitant administration.

4. The composition according to claim 1, wherein the timolol is in the form of timolol maleate.

5. The composition according to claim 4, wherein the timolol moiety of the timolol maleate is in a concentration of 0.5 w/v %.

6. A composition for lowering intraocular pressure comprising 0.001 to 0.1 w/v % of isopropyl (6-{[4-(pyrazol-1-yl)benzyl](pyridin-3-ylsulfonyl)aminomethyl} pyridin-2-ylamino)acetate and 0.1 to 0.5 w/v % of timolol, in a combined pharmaceutically effective amount, wherein the isopropyl (6-{[4-(pyrazol-1-yl)benzyl](pyridin-3-ylsulfonyl)aminomethyl}pyridin-2-ylamino)acetate may be in the form of a salt thereof, and the timolol may be in the form of a salt thereof.

7. The composition according to claim 6, wherein the composition is obtained by mixing isopropyl (6-{[4-(pyrazol-1-yl)benzyl](pyridin-3-ylsulfonyl) aminomethyl}pyridin-2-ylamino)acetate or a salt thereof and timolol or a salt thereof.

8. The composition according to claim 6, wherein the composition is obtained by providing a separate preparation for each of isopropyl (6-{[4-(pyrazol-1-yl)benzyl](pyridin-3-ylsulfonyl)aminomethyl}pyridin-2-ylamino)acetate or a salt thereof and timolol or a salt thereof, for a concomitant administration.

9. The composition according to claim 6, wherein the timolol is in the form of timolol maleate.

10. The composition according to claim 9, wherein the timolol moiety of the timolol maleate is in a concentration of 0.5 w/v %.

11. A method for treating glaucoma or ocular hypertension or for lowering interocular pressure comprising (i) administering to a patient in need thereof a pharmaceutically effective amount of a composition comprising 0.001 to 0.1 w/v % of isopropyl (6-{[4-(pyrazol-1-yl)benzyl](pyridin-3-ylsulfonyl)aminomethyl}pyridin-2-ylamino)acetate and 0.1 to 0.5 w/v % of timolol or (ii) concomitantly individually administering to a patient in need thereof 0.001 to 0.1 w/v % of isopropyl (6-{[4-(pyrazol-1-yl)benzyl](pyridin-3-ylsulfonyl)aminomethyl} pyridin-2-ylamino)acetate and 0.1 to 0.5 w/v % of timolol, in a combined pharmaceutically effective amount, wherein the isopropyl (6-{[4-(pyrazol-1-yl)benzyll (pyridin-3-ylsulfonyl)aminomethyl} pyridin-2-ylamino)acetate may be in the form of a salt thereof, and the timolol may be in the form of a salt thereof.

12. The method according to claim 11, wherein the method is for treating glaucoma or ocular hypertension.

13. The method according to claim 12, wherein the glaucoma is a condition selected from the group consisting of primary open angle glaucoma, normal tension glaucoma, hypersecretion glaucoma, acute angle-closure glaucoma, chronic angle-closure glaucoma, combined-mechanism glaucoma, steroid-induced glaucoma, amyloid glaucoma, neovascular glaucoma, malignant glaucoma, capsular glaucoma and plateau iris syndrome.

14. The method according to claim 11, wherein the timolol is in the form of timolol malteate.

15. The method according to claim 12, wherein the timolol is in the form of timolol maleate.

16. The method according to claim 14, wherein the timolol moiety of the timolol maleate is in a concentration of 0.5 w/v %.

17. The method according to claim 15, wherein the timolol moiety of the timolol maleate is in a concentration of 0.5 w/v %.

* * * * *